(12) United States Patent
Hougham

(10) Patent No.: US 6,404,491 B1
(45) Date of Patent: *Jun. 11, 2002

(54) ROLLING MULTIPLE INTERNAL REFLECTION SPECTROSCOPY

(75) Inventor: Gareth Geoffrey Hougham, Ossining, NY (US)

(73) Assignee: International Business Machines Corporation, Armonk, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/960,828

(22) Filed: Oct. 30, 1997

(51) Int. Cl.⁷ .................................................. G01J 3/42
(52) U.S. Cl. ........................ 356/300; 356/244; 356/429; 250/339.11
(58) Field of Search ............................. 356/300, 244, 356/429; 250/339.11, 339.12

(56) References Cited

U.S. PATENT DOCUMENTS

| | | | |
|---|---|---|---|
| 2,466,615 A | * 4/1949 | Rusca et al. | 356/429 |
| 3,460,893 A | * 8/1969 | Wilks | 356/300 |
| 4,124,300 A | * 11/1978 | Mead et al. | 356/429 |
| 4,595,833 A | 6/1986 | Sting | |
| 4,818,710 A | * 4/1989 | Sutherland et al. | 356/445 |
| 4,988,195 A | 1/1991 | Doyle | |
| 5,200,609 A | 4/1993 | Sting et al. | |
| 5,220,401 A | 6/1993 | Milosevic et al. | |
| 5,754,722 A | * 5/1998 | Melling | 356/436 |

* cited by examiner

Primary Examiner—F L Evans
(74) Attorney, Agent, or Firm—Thomas A. Beck; Daniel P. Morris

(57) ABSTRACT

A structure is described having an optical element having a cylindrical shape adapted for rolling in contact with a surface of a material, a source of electromagnetic radiation coupled into one portion of the cylinder to interact with the surface, and exiting at another portion of the optical element for detection. An apparatus is described for applying electromagnetic radiation to a surface having a cylindrical roller formed from a material transmissive to the electromagnetic radiation; the cylindrical roller adapted for rolling on the surface; and the cylindrical roller adapted for receiving the electromagnetic radiation for reflecting the electromagnetic radiation therein and for directing the electromagnetic radiation towards a detector for detection. The structure and apparatus is directed for use with in-line or real-time process monitoring technology. More particularly to the problem of real-time spectroscopic determination of degree of chemical and physical changes to materials, in particular sheet materials, on a moving fabrication line. In many continuous-feed manufacturing processes involving sheet materials, monitoring the degree of chemical reaction and desiccation is essential and often problematic. Remote sensing is often not possible due to the speed of material flow, or the necessity for sensor-element/sample contact. Many prior attempts to commercialize real-time monitoring systems have performed marginally or were useful under only a narrow range of circumstances.

3 Claims, 4 Drawing Sheets

ROLLING MULTIPLE INTERNAL REFLECTION SPECTROSCOPY

BACKGROUND OF THE INVENTION

1. Field of the Invention

An apparatus for applying electromagnetic radiation to a surface such as the surface of a moving sheet of material by directing electromagnetic radiation towards a cylindrical roller which rolls on the surface and collecting and detecting electromagnetic radiation emerging from the roller.

2. Discussion of Prior Art

The present invention is directed to in-line or real-time process monitoring technology. More particularly to the problem of real-time spectroscopic determination of degree of chemical and physical changes to materials, in particular sheet materials, on a moving fabrication line. In many continuous-feed manufacturing processes involving sheet materials, monitoring the degree of chemical reaction and desiccation is essential and often problematic. Remote sensoring is often not possible due to the speed of material flow, or the necessity for sensor-element/sample contact. Many prior attempts to commercialize real-time monitoring systems have performed marginally or were useful under only a narrow range of circumstances. Most in-line spectroscopic methods are applicable to liquids where a flowing liquid sample moves through a light beam confined to a narrow and well defined optical cell which has been engineered to sit stationary within the flowing medium (Sting, D. W. Multiple Internal Reflection Cell Optical System for use in Infrared Spectroscopy for Liquid and Fluidized samples; Sting, D. W., Ed.; Sting, D. W.: USA, (1983) and (Milosevic, M. Multiple Internal Reflection Liquid Sampling; Milosevic, M., Ed.: USA). There are few instrumental methods which address the real-time infrared (or other wavelength range) spectroscopic determination of a moving solid sample. There are few optical arrangements which lend themselves to moving samples, most of them being non-contact in nature. Transmission infrared (or other) spectroscopy can be used only in cases where the sample is thin enough and non-absorbing enough so that the total absorption is not significantly greater than 1 (A=-log l/lo). At this point the linear relationship between peak attenuation and bond species concentration (Beer-Lambert law) no longer holds. Only extremely thin free-standing polymer films would be measurable by this transmission method. A great many sheet products would be too thick and too absorbing to be measurable by this technique. Another non-contact method is direct reflection from the moving sheet material. There are two variations on this: specular (mirror-like) and diffuse reflection. In the first, a beam of infrared (or other) light is impinged at an angle to the sheet, the light interacts with the sample and reflects. The reflected beam is directed to the detector. The first problem with this technique is that few materials are smooth enough to reflect in a specular way. Further, in the case of infrared spectroscopy very little light is generally reflected due to strong absorption of an infrared beam by most organic substances. For both reasons, too little light is reflected to enable a spectroscopic measurement of high enough quality for quantitative determination of bond concentrations.

In the case of sample types which are too rough to allow specular reflection (most samples), the light is reflected in a diffuse and scattered manner further burdening the collection of adequate reflected light to enable spectroscopic determination of the sample state. In this case a collection of concave mirrors are assembled to try to collect and recolumnate the scattered light; but rarely is the quality of the spectrum adequate for quantitative purposes.

Cylindrical cell types for multiple internal reflection have been used primarily for liquid analysis (Doyle, W., M., Internal Reflection Apparatus and Method Using Cylindrical Elements, (1989)). Diamond has been used for MIR spectroscopy (Sting, D.; Reffner, J. Radiant Energy Spectroscopy with Diamond Internal Reflection Element; Sting, D.; Reffner, J., Ed., (1993)), but not in thin film form. MIR has also been used in process monitoring applications (Stevenson, W. A. Monitoring Technology; Stevenson, W. A., Ed., (1987)). Several other uses for multiple internal reflection are known (Harrick, N. J., Multiple Internal Reflection, 3rd ed., John Wiley and Sons, (1967, 1987)).

No prior art examined has identified the use of MIR spectroscopy for moving sheet samples using cylindrical elements made or allowed to rotate with the sample, as described herein.

BRIEF DESCRIPTION OF THE DRAWINGS

Further objects, features, and advantages of the present invention will become apparent from a consideration of the following detailed description of the invention when read in conjunction with the drawings FIG's. in which.

SUMMARY OF THE INVENTION

Figure 1:
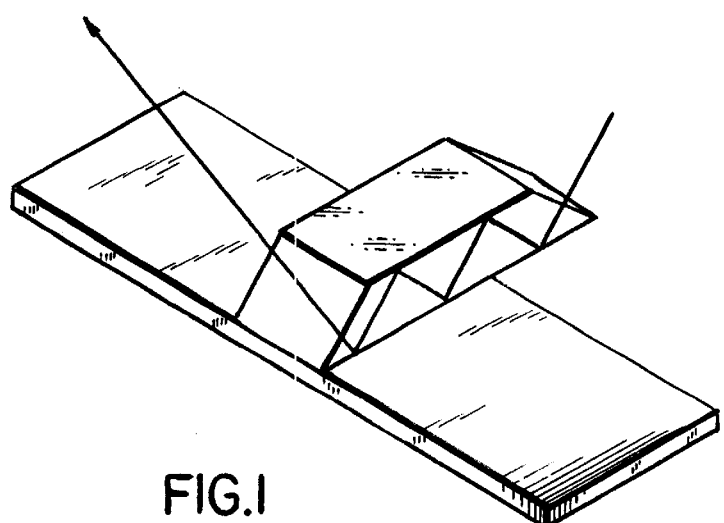
FIG. 1—Standard MIR (multiple internal reflection spectroscopy) element in contact with immobile sheet sample.

A broad aspect of the present invention is a structure having an optical element having a cylindrical shape adapted for rolling in contact with a surface of a material, a source of electromagnetic radiation coupled into one portion of the cylinder to interact with the surface, and exiting at another portion of the optical element for detection.

Another aspect of the present invention is an apparatus for applying electromagnetic radiation to a surface having a cylindrical roller formed from a material transmissive to the electromagnetic radiation; the cylindrical roller adapted for rolling on the surface; and the cylindrical roller adapted for receiving the electromagnetic radiation for reflecting the electromagnetic radiation therein and for directing the electromagnetic radiation towards a detector for detection.

DETAILED DESCRIPTION

Described herein is a technique for real-time monitoring of sheet material fabrication using attenuated total reflection spectroscopy (ATR) in a new configuration. ATR is often referred to by the synonymous phrase "Multiple Internal Reflection" or MIR. The ATR or MIR methods are most often used in infrared spectroscopy, and in the last few years most often in conjunction with Fourier Transform Infrared Instruments (Harrick, N. J., Multiple Internal Reflection, 3rd ed., John Wiley and Sons, (1967, 1987)). The science behind ATR spectroscopy is well understood, yet its application beyond the laboratory is relatively rare. The standard ATR methods are time consuming to perform, awkward, and off-line (static) by nature.

This invention changes the geometry of typical MIR spectroscopic elements to enable real-time spectroscopic measurements while retaining the necessary intimate physical contact between element and sample.

As an example of how this invention may be used, industrial preparation of epoxy prepreg is illustrative. In the fabrication of epoxy prepreg sheet material, intended for later circuit board manufacturing, a roll of woven glass cloth, mounted on a roller at the beginning of the treater tower, is unwound, dipped into epoxy solution and passed into ovens to remove the solvent and initiate chemical cross linking. After emerging from the ovens, the sheet prepreg is again wound up onto a roll. The degree of chemical crosslinking and solvent removal must be carefully controlled to ensure proper prepreg sheet properties. This is called B-stage endpoint detection. Endpoint detection is traditionally accomplished by cutting prereg material from the moving web and performing off-line measurements, including melt-flow and spectroscopic measurements. Tuning the treater tower to produce properly B-staged prepreg requires a great deal of time and results in substantial material loss.

The development of on-line methods to help tune treater towers to specification is a field of intense research in order to try to reduce material and time losses. Similar considerations apply in other sheet manufacturing processes.

The current invention addresses this problem by extending the ATR spectroscopic technique to geometries which allow continuous on-line measurement. No cutting of product or off-line measurements are required. This will speed the process of treater tower, or other process, tuning and will lead to substantial improvements in process efficiency and product throughput.

The standard ATR spectroscopy technique is illustrated in FIG. 1, in its most common use with Fourier transform infrared spectroscopy. An optical element is placed in contact with the sample and light pressure is applied by clamp. Infrared light is introduced to one face of the element at an angle below the angle of internal reflection. The light reflects inside back and forth between the two parallel optical faces, and is absorbed by the sample on each reflection at frequencies characteristic of the sample and its state of cure. The light then emerges at the end of the optical element and is directed to the detector.

Figure 2:
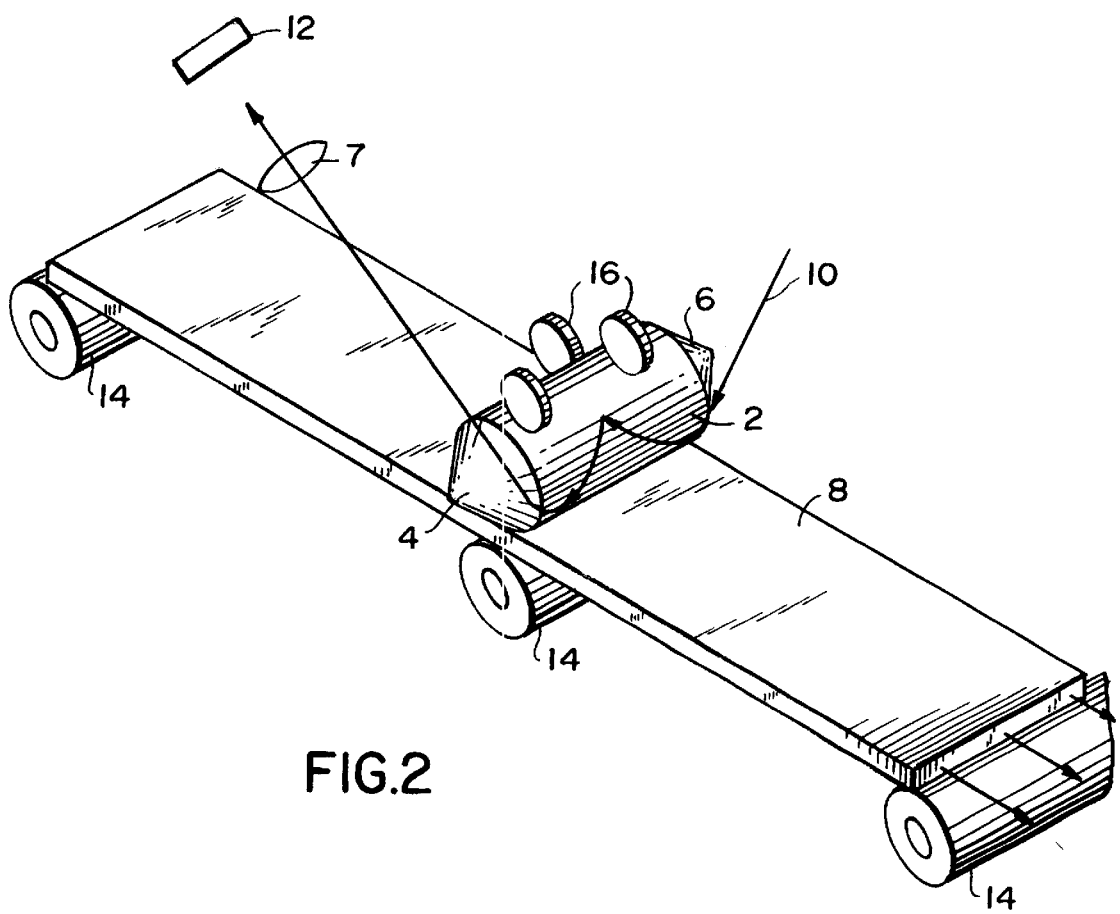
FIG. 2—Isomeric view of ROMIR assembly
Figure 3A:
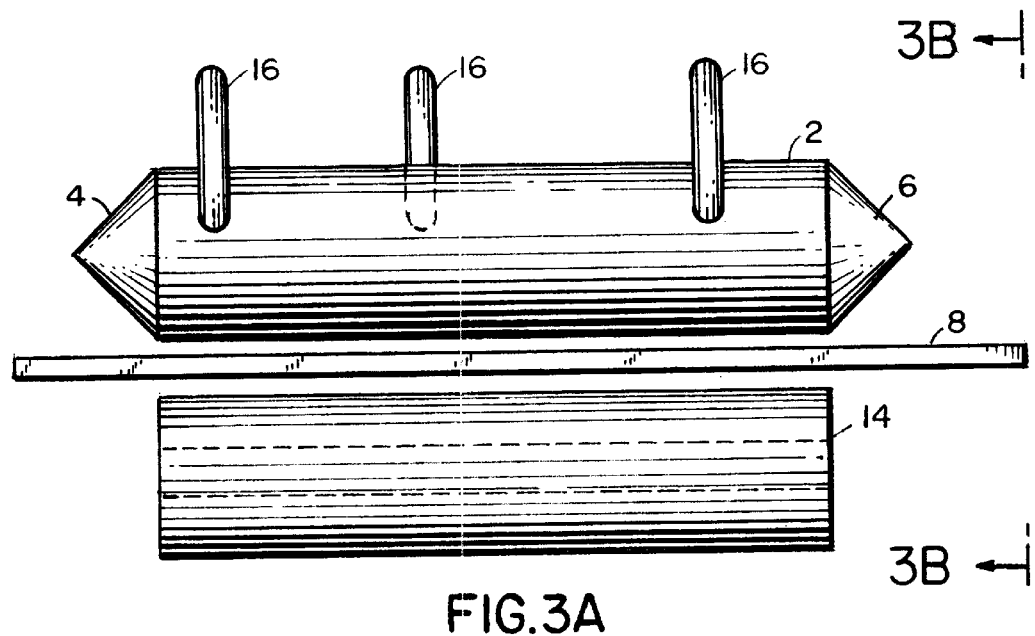
FIG. 3—Rolling Multiple Internal Reflection (ROMIR) element shown with 3 alignment rollers above and 1 counter pressure roller below sample sheet.
Figure 3B:
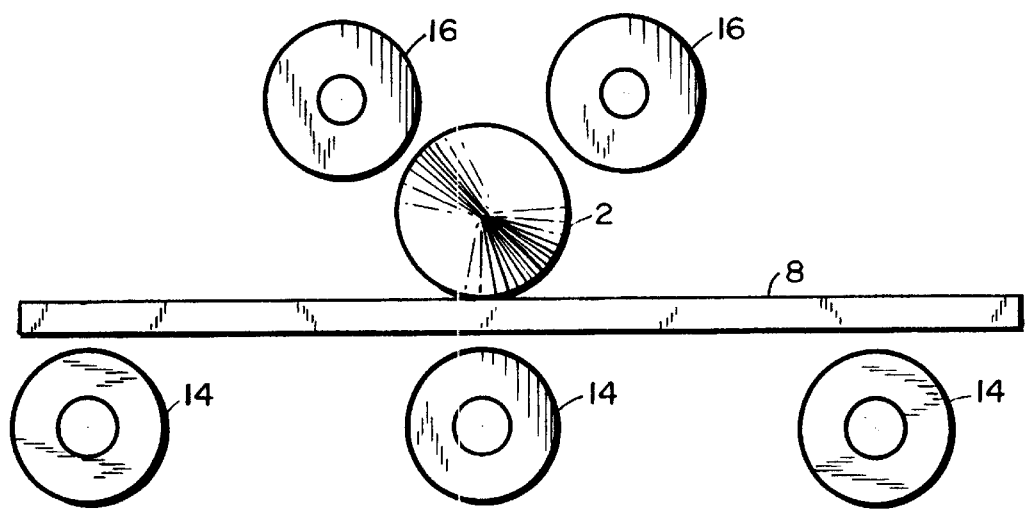

The present invention extends this technique to moving sample substrates by replacing the parallelepiped optical element with one that is preferably cylindrical with preferably two conical ends. This is illustrated in FIGS. 2 and 3. This cylindrical element rotates as the sheet sample moves below it. Spectroscopic measurement is performed as the cylinder rotates at substantially the same rate at which the sample passes by.

The simplest embodiment of the present invention is shown in sketch form in FIG. 2 and also FIG. 3. The optical element 2 is a cylindrically shaped infrared (or other wavelength) transparent element which may also have conical shaped ends 4, and 6 to enable light to enter and exit the element at a desired angle. The sheet sample under investigation 8 may be moving in a direction perpendicular to the axis of rotation of the cylindrical optical element 4. Infrared exitation light is introduced to one end of the element at an angle below that for total internal reflection. It reflects back and forth inside the optical element until reaching the end at which point it exits the element and is directed by other optics 7 to the detector. It is during the time that the (preferably infrared) light is internally reflecting that it interacts with the sample via what is called an evanescent wave which penetrates beyond the element-sample interface only a small distance. This small penetration distance is angle, frequency, and refractive index-dependent, but is usually of the order of microns.

Thus the absorption of the infrared light is kept relatively small allowing adequate light to provide a strong signal to the detector 12. In order for the evanescent wave to interact with the sample despite this penetration depth of only microns, intimate contact between the element 4 and sample 8 must be maintained. This is done by applying a slight pressure via the alignment rollers 16 and the counter pressure roller 14 on the other side of the sample. Thus, as the sheet sample moves, the optical element rolls to maintain good mechanical contact while avoiding slippage. The infrared signal is collected and averaged for a time period to provide a quality spectrum.

FIG. 3 shows a front view and side view of the same assembly as FIG. 2, with some illustrative dimensions shown to provide a concept of the order-of-magnitude of the anticipated sizes. These sizes are for illustration purposes only, and assemblies which are both larger and smaller are anticipated for different applications.

EXAMPLE EMBODIMENT

A germanium or ZnSe cylindrical optical element is brought into contact with an epoxy prepreg sheet near the end of the prepreg treater tower. The element is rotated at the same rate as the moving sheet material and a slight pressure is maintained to ensure good optical contact. An infrared beam is focussed into one conical end of the element; it interacts with the sample and characteristic frequencies are selectively absorbed. The partly attenuated beam exits the element from the opposite conical end and is focussed to the infrared detector. An infrared spectrum is thus obtained without interruption of the movement of the sample traveling between treater tower rollers.

Geometry of Cylinders

Optical element geometry in ROMIR is cylindrical. For most applications, the cylinder will be capped on both ends with conical sections to facilitate light entry at angles necessary for internal reflection. This angle will be dependent on both the chemical composition of the element with its characteristic refractive index and on the chemical composition of the sample with which it is in contact. Below the angle necessary for internal reflection, shallower angles may be used to control the number of reflections between light ingress and egress.

The primary geometry of the optical element for use with infrared radiation is cylindrical with two conical ends. The size can range from very small with diameters of one mm and lengths of a couple inches, to larger where the diameter is on the order of inches and the length up to a foot or more. The lower limit is determined by external factors such as mechanical limitations of gearing to propel the rotation and such factors as the surface roughness of the sample. Rough surfaces may require larger diameters to allow smooth rotation. The upper size limits are determined by intrinsic absorption of the light by the optical element itself. Typically, in infrared spectroscopy utilizing ATR elements, optical losses become severe within a maximum of about 5 cm optical travel.

In cases where light wavelength ranges other than the infrared are to be used, such as visible range, many materials exist where no upper length boundary exists. An example would be quartz where optical transmission will not be a limiting factor for most conceivable designs. Optical elements as long as the sample web is wide would be easily accommodated.

There are other instances where simple solid cylinders may be used with light impinging at an angle to the circular cross section. Still other instances may call for the use of hollow cylinders, where light is introduced to edge of the cylindrical shell. Similarly, composite cylinders may be used where the inner cylinder is for mechanical support while an outer cylinder is used as the multiple internal reflection element. This outer cylinder can be comprised of a machined hollow cylinder or a coating applied to an inner core cylinder. Such a coating could be an organic polymer applied in any number of ways which would act as a waveguide. Such a coating could also consist of any number of inorganic solids which are transparent to the wavelength range of interest.

Further, other means of introducing light to a thin film cylindrical shell may at times be necessary to utilize the ROMIR technique under certain circumstances. If for instance a wide diameter ROMIR element were desired rendering a solid optical element too costly or otherwise unacceptable, a mechanically durable core cylinder, illustrated in FIG. 5 as 54 could be fabricated such that a thin transparent coating 50 would be applied and a circular coupling prism 52 with the geometry of a ring attached to the ends of the element to aid in efficient light coupling and decoupling. In order to accommodate the thickness of the prism, the roller may have to taper to a narrower diameter at the extreme ends to allow clearance between the prism and the sample. If the ROMIR element is wider than the sample web, then this tapering would be unnecessary as the prism rings could hang over the edge and avoid direct mechanical contact.

Figure 5:
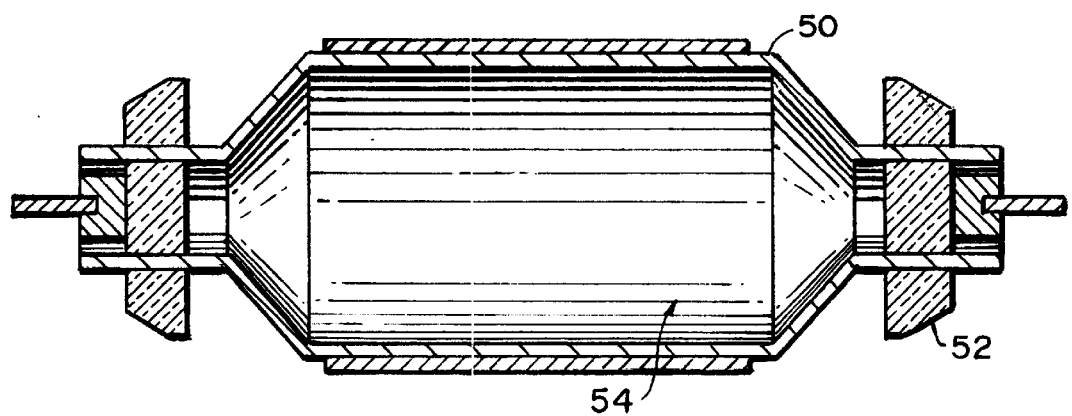
FIG. 5—Solid Core ROMIR assembly.
Figure 6:
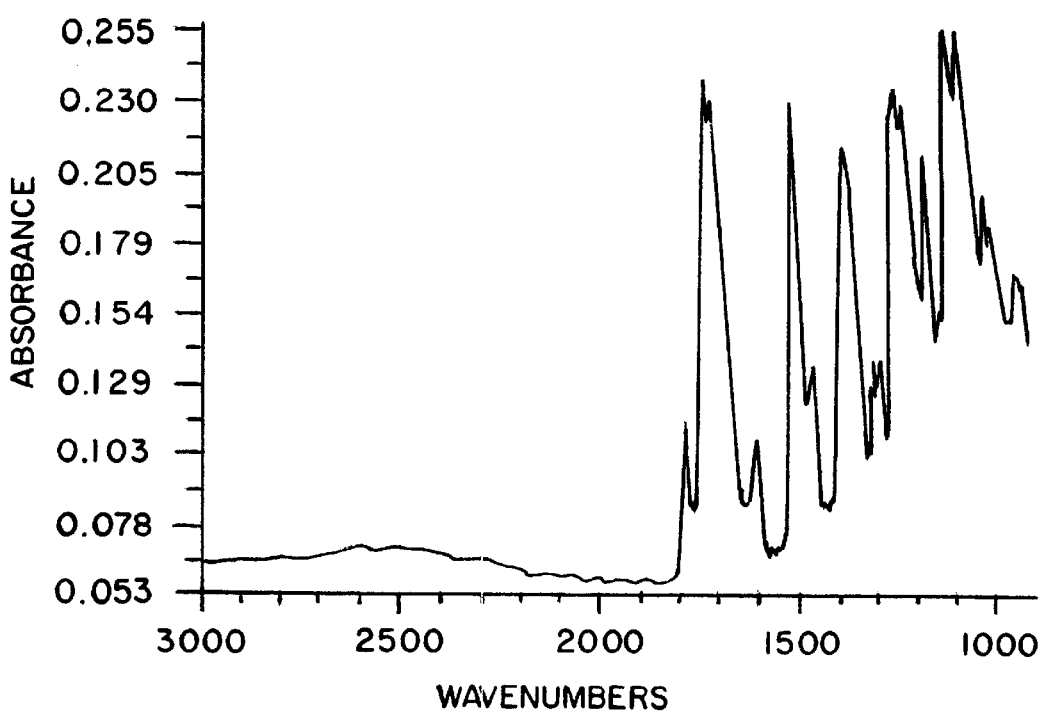
FIG. 6—Experimental infrared spectrum of Kapton Polyimide obtained through cylindrical optical element in contact with sheet Kapton sample.

Still other instances may involve more complex composites. For example, a solid core may have a waveguide coating or outer shell such as ZnSe, followed by another coating of very thin abrasion resistant material, which is transparent to the wavelength of interest, such as CVD diamond. (56) An example of a composite ROMIR element such as this is shown in FIG. 5.

Abrasion Abatement

Optical element degradation by abrasive sheet substrates is anticipated. Chemical vapor deposition diamond coating of the optical element will mitigate element degradation in most applications.

Figure 4A:
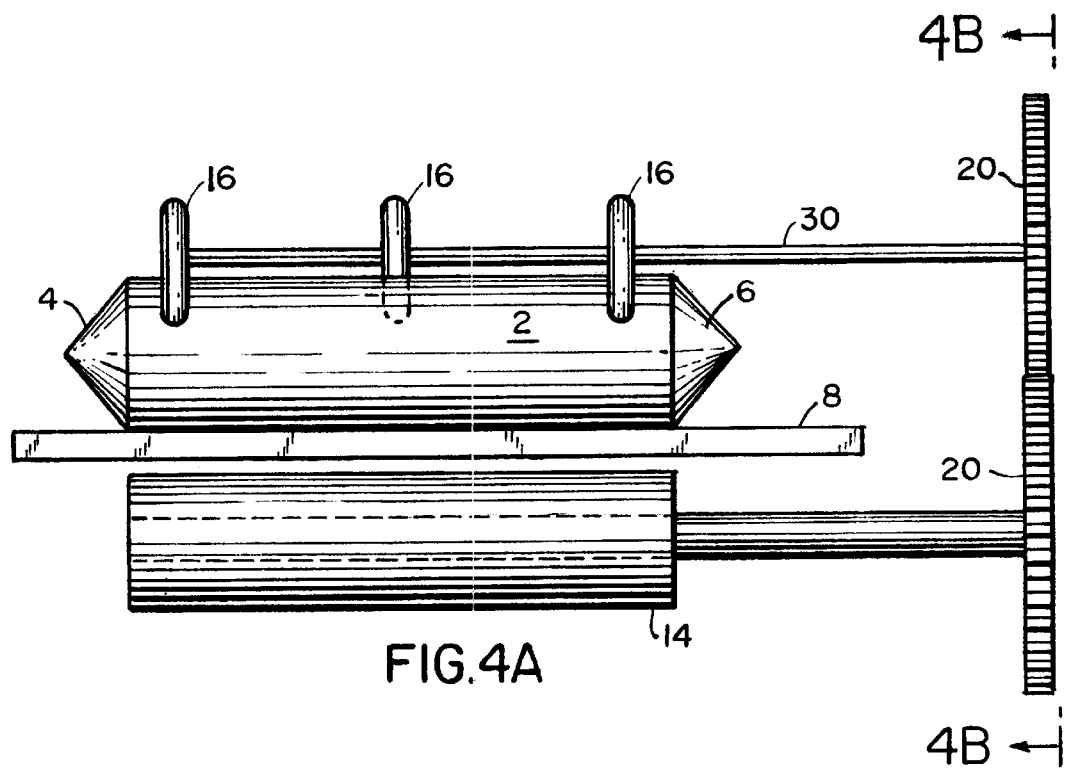
FIG. 4—ROMIR assembly shown with drive mechanism common to element and counter roller to ensure cosynchronous motion.
Figure 4B:
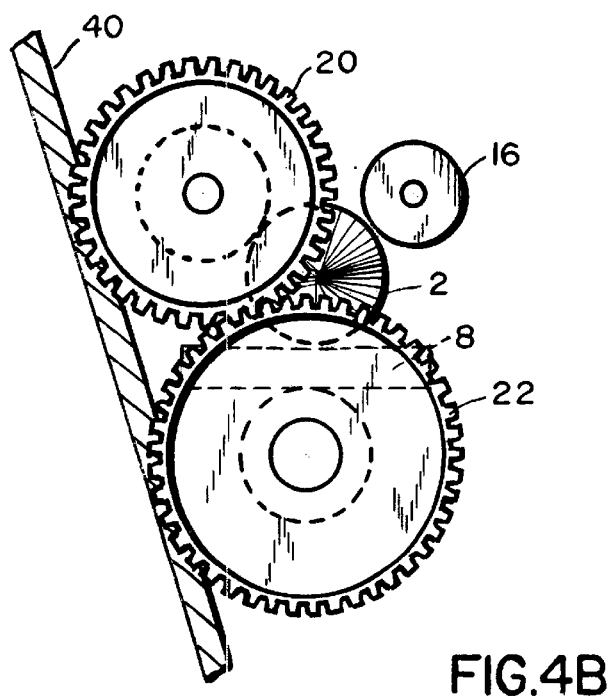

The optical element is designed for synchronous rotation with a moving sample. One application would have the optical element driven by the moving sample itself, as implied in FIGS. 2 and 3, ensuring continuous and coterminous element/sample proximity. However, this may result in significant abrasion. Another method would have the optical element rotation mechanically assisted by auxiliary motors, or by mechanical coupling with the moving sample through a gearing mechanism. This is illustrated in FIG. 4 in a general way. In FIG. 4 the bottom counter pressure roller and the drive and alignment roller wheels are mechanically linked via gearing mechanisms to ensure synchronous rotation. These could be driven by a common motor or mechanical linkage, or be coupled in series. The drawing in FIG. 4 is schematic only and intends to show only that these rotations are coupled.

In FIG. 4, many of the mechanical components are the same as those for the simple design of FIGS. 2 and 3 with the addition of the mechanical driving mechanisms which consist of a gear 20 to drive the alignment and drive wheel axle 30, and a gear to drive the counter pressure roller 22. In addition, a spline gear 40 is shown which would be used in the case where both the gears 20 and 22 would be driven by a third mechanical element such as a motor or a mechanical link to another rotating part of the system. The sizes of the gears are for illustration only and would in a real device be designed to provide identical rates of movement of the outer circumference surface of the optical element and the counter pressure rollers—the two mechanical elements in direct contact with the sample.

In these ways, the rate of rotation would be made to exactly or closely match the rate of prepreg translation, thus minimizing abrasive slippage Alignment Roller Design The rollers or wheels used to apply pressure against the rotating optical element should be compliant materials like rubber. However, care must be exercised to choose materials, which have infrared spectras outside of the range of interest.

The choice of materials for the alignment rollers is important. Since these rollers contact the optical element directly, care must be exercised to choose materials that have both desirable mechanical and spectroscopic properties. The infrared beam bouncing within the optical element will be selectively absorbed by both the sample sheet and these rollers. In order that the ultimate spectrum not reflect the chemical composition of these rollers a background spectrum with only the rollers in place should be taken. This background spectrum is then ratioed to the sample spectrum to remove the spectral features of the rollers. Alternatively, the background spectrum may be subtracted. These are standard practices in infrared and other spectroscopic techniques. This process will be made easier and more effective however, if the spectral characteristics of the rollers are distinct from the sample. Thus, elastomeric rollers (rubber wheels) made from inorganic or largely inorganic elastomers may provide some advantages. Examples of such materials would be siloxane and polyphosphazine based polymers.

Other Wavelengths

The methods described here can be used for many radiation wavelength ranges other than infrared. Ultraviolet and visible radiation can be used, with the primary difference being the chemical composition of the optical element. For this wavelength range, materials such as quartz would be appropriate. Near and far infrared are also known to be very useful for spectroscopic determinations relevant to sheet curing. Other wavelength ranges are also expected to be applicable to this ROMIR technique.

The wavelength chosen for a particular application would depend on the specific spectroscopic information sought. Infrared in the fingerprint region provides detailed and quantitative measurement of the growth and attenuation of bond-specific absorption. But, the means of delivering the excitation beam is inconvenient and requires sealed or nitrogen-purged tubes. In other infrared ranges, flexible optical fibers can be used. It is to be understood that many other wavelength ranges can be used and that each may require some special design considerations for both the element and the means of bringing the radiation to and from the element.

The information provided by the UV-Vis range, is most valuable when the chemical reaction being followed involves a change in concentration of chromophores in this frequency range.

Further, there will be instances where monochromatic sources will be useful in the ROMIR technique. Laser radiation of specific frequencies can be used to monitor specific absorption changes.

There may be times when optical coatings on the inside of the cylinder will provide advantages in the coupling of light into and out of the cylindrical shell element.

FIG. 5 shows an infrared spectrum of Kapton™, a common polyimide produced by Dupont. This spectrum was obtained on a Nicolet Infrared Spectrometer configured to simulate a ROMIR assembly. This consisted of a cylindrical optical element machined from ZnSe pressed in a clamp against a thin sheet of polyimide. The infrared beam was directed into the optical element at an angle normal to the 45° conic end.

The light exiting the crystal was collected via a simple plane mirror and reflected to the detector. No special mirror assemblies were used to collect the majority of light exiting from other angles of the conic endpoint of the optical element, as it would in an optimal configuration.

The quality of this polyimide spectrum is very high with ample signal to noise ratio, and very good peak symmetry and shape. This spectrum thus demonstrates the viability of the spectroscopic aspects of the invention and only the mechanical engineering to provide synchronous movement of the sample and optical elements remains un-built as a prototype.

Refractive index by incorporating moving source and detector optics to measure the Critical angle.

All references cited in this application herein are incorporated by reference herein.

While this invention has been particularly shown and described with respect to the preferred embodiment thereof, it will be understood by those skilled in the art that the foregoing and other changes in form as details may be made therein without departing from the spirit and scope of the invention.

What is claimed is:

1. An apparatus for applying electromagnetic radiation to a moving sheet of epoxy prepreg material to measure the extent of chemical cure of said moving sheet of epoxy prepreg material, said moving sheet of epoxy prepreg material having a top and bottom surface;

said apparatus comprising:

a feeder for feeding said moving sheet of epoxy prepreg material;

a collector for collecting said moving sheet of epoxy prepreg material;

an optical element, comprising a solid, cylindrical mechanically durable inner core roller having an exterior surface with a thin coating of transparent material secured thereon;

said optical element having a top and a bottom and two conical ends, said thin coating of transparent material on said exterior surface of said inner core formed of a material selected from the group consisting of organic polymer or inorganic solids transmissive to said electromagnetic radiation, said electromagnetic radiation comprising the light wavelength ranges;

said optical element disposed between said feeder and said collector; and said optical element being adapted for rolling on said top surface of said moving sheet of epoxy prepreg material at a speed;

means for controlling the rotation speed of said optical element to synchronize said optical element speed with the speed of said moving sheet of epoxy prepreg material;

a plurality of alignment roller wheels arranged in staggered position forward and laterally with respect to one another and applying pressure against said top of said optical element so that said optical element contacts said moving sheet of epoxy prepreg material, said alignment rollers formed from an elastomer selected from the group consisting of siloxane and polyphosphazine:

a counterpressure roller contacting said bottom of said sheet of epoxy prepreg material so that there is the necessary physical contact between said sheet of epoxy prepreg material and said bottom of said optical element;

a circular coupling prism attached adjacent each said conical end of said optical element;

a source for directing said electromagnetic radiation into said thin coating of transparent material on said exterior surface of said inner core at an input location at an angle below that for total internal reflection so that said electromagnetic radiation internally reflects within said thin coating of transparent material and determines the refractive index of said material using a critical angle technique wherein said radiation exits from said thin coating of transparent material on said exterior surface of said inner core cylinder at an output location;

a detector positioned to receive said electromagnetic radiation exiting said thin coating of transparent material on said exterior surface of said inner core, said radiation detected by said detector providing the degree of chemical and physical changes of said epoxy prepreg material.

2. An apparatus according to claim 1 wherein said feeder is a feed roller and said collector is a collector roller.

3. An apparatus according to claim 1 wherein said electromagnetic radiation multiply internally reflects within said optical element by being directed into said optical element so that electromagnetic radiation is incident on optical element to be substantially totally internally reflected.

* * * * *